(12) United States Patent
Peltier

(10) Patent No.: US 8,460,208 B2
(45) Date of Patent: Jun. 11, 2013

(54) FLASK FOR PREPARING A CYTOLOGICAL SUSPENSION BASED ON A FIXING SOLUTION

(75) Inventor: Eric Peltier, Clamart (FR)

(73) Assignee: Novacyt, Velizy-Villacoublay (FR)

( * ) Notice: Subject to any disclaimer, the term of this patent is extended or adjusted under 35 U.S.C. 154(b) by 0 days.

(21) Appl. No.: 13/357,127

(22) Filed: Jan. 24, 2012

(65) Prior Publication Data

US 2012/0122202 A1  May 17, 2012

Related U.S. Application Data

(62) Division of application No. 11/014,865, filed on Dec. 20, 2004.

(30) Foreign Application Priority Data

Dec. 18, 2003  (FR) ..................... 03 14907

(51) Int. Cl.
| | |
|---|---|
| *A61B 10/00* | (2006.01) |
| *B01D 24/00* | (2006.01) |
| *B01D 35/24* | (2006.01) |
| *B01D 24/38* | (2006.01) |
| *C12M 1/34* | (2006.01) |

(52) U.S. Cl.
USPC ........... 600/569; 210/348; 210/353; 210/455; 210/464; 210/466; 435/287.1; 600/562

(58) Field of Classification Search
USPC ................ 435/287.1; 600/569; 210/348, 353, 210/455, 464, 466
See application file for complete search history.

(56) References Cited

U.S. PATENT DOCUMENTS

| | | | |
|---|---|---|---|
| 3,815,580 | A | 6/1974 | Oster |
| 4,305,303 | A | 12/1981 | Thies |
| 4,318,803 | A | 3/1982 | Holmgren |
| 4,321,139 | A | 3/1982 | Auclair |
| 4,378,611 | A | 4/1983 | Ninehouser |
| 4,439,319 | A | 3/1984 | Rock |
| 5,104,533 | A | 4/1992 | Szabados |
| 5,192,504 | A | 3/1993 | Cassaday |
| 5,370,128 | A | 12/1994 | Wainwright |
| 5,422,273 | A | 6/1995 | Garrison |
| 5,518,612 | A | 5/1996 | Kayal |
| 5,532,168 | A | 7/1996 | Marantz |
| 5,575,914 | A | 11/1996 | Jeyendran |
| 5,593,587 | A | 1/1997 | Fumihiko |
| 5,601,728 | A | 2/1997 | Kayal |
| 5,711,875 | A | 1/1998 | Kayal |
| 6,045,013 | A | 4/2000 | Yang |
| 6,129,214 | A | 10/2000 | Bar-Ami |
| 6,291,234 | B1 | 9/2001 | Raz |
| 6,346,087 | B1 | 2/2002 | Peltier |
| 6,395,233 | B1 | 5/2002 | Diamond |
| 6,521,190 | B1 | 2/2003 | Edens |
| 2008/0164200 | A1 | 7/2008 | Pressman |

FOREIGN PATENT DOCUMENTS

| | | |
|---|---|---|
| EP | 0 520 408 | 12/1992 |
| FR | 2 792 331 | 10/2000 |

*Primary Examiner* — Sean Dougherty
(74) *Attorney, Agent, or Firm* — Young & Thompson

(57) ABSTRACT

A system for preparing a cytological suspension is based on a fixing solution. The system containing a cytological sample-taking brush and a flask having an opening for receiving the cytological sample-taking brush are detachably fastened to a handle including a brush-receiving filter basket that is at least partially immersed in the a suspension.

14 Claims, 3 Drawing Sheets

FLASK FOR PREPARING A CYTOLOGICAL SUSPENSION BASED ON A FIXING SOLUTION

CROSS REFERENCE TO RELATED APPLICATIONS

This application is a division of copending application Ser. No. 11/014,865 filed on Dec. 20, 2004 which claims priority to French application 0314907 filed on Dec. 18, 2003. The entire contents of each of the above-identified applications are hereby incorporated by reference.

BACKGROUND OF THE INVENTION

The present invention relates to a flask for preparing a cytological suspension based on a fixing solution.

DESCRIPTION OF THE RELATED ART

Such flasks are used in the prior art for preparing cervical or vaginal cytological suspensions for analysis.

Practitioners take cervical or vaginal samples using special brushes that are detachably secured to handles for manipulating them.

Once the sample has been taken, the practitioner plunges the brush into the flask and detaches the brush from the handle, so as to enable the cells that have been taken to become deposited in the fixing solution.

Nevertheless, undesirable components can also become deposited in the fixing solution, such as, for example: debris recovered by the brush while taking the sample (mucus, aggregations, etc. . . . ), squamae coming from the practitioner that become deposited in the flask, in particular during handling of the brush in order to detach the handle, etc.

Unfortunately, those components can be very troublesome during subsequent analysis of the suspension.

The Applicant has already proposed a special flask structure in an attempt to solve those problems.

That flask is described in document FR-A-2 792 331.

According to that document, the flask is provided with an opening for receiving a cytological sample-taking brush that is detachably secured to a handle, and the opening of the flask includes abutment means for the brush, enabling it to be held in the flask and enabling it to be detached from the handle, and at least a perforated portion of web for filtering the suspension while pouring.

Nevertheless, in use, such a flask has also presented a certain number of drawbacks, in particular with the perforated portion of web for filtering the suspension becoming clogged with the above-mentioned components.

SUMMARY OF THE INVENTION

The object of the invention is thus to further improve such preparation flasks.

To this end, the invention provides a flask for preparing a cytological suspension base on a fixing solution, the flask being provided with an opening for receiving a cytological sample-taking brush that is detachably fastened to a handle, the flask including a brush-receiving filter basket that is at least partially immersed in the suspension.

According to other characteristics:
the filter basket is detachably fastened inside the flask so as to enable it to be withdrawn, and thus enabling the brush to be withdrawn and the suspension to be recovered;
the basket is screwed into the flask;
the basket and the flask include spring catch means;
the bottom of the flask is provided with means for draining out the suspension;
the flask comprises two portions that are secured to each other in detachable manner, the top portion carrying the filter basket and the bottom portion containing the suspension, thereby enabling it to be recovered;
the two portions of the flask include complementary screw fastener means; and
a portion of the filter basket is situated outside the suspension and includes a hole through which the suspension can be recovered by pouring or by suction.

BRIEF DESCRIPTION OF THE DRAWINGS

The invention will be better understood on reading the following description given purely by way of example and made with reference to the accompanying drawings, in which.

DETAILED DESCRIPTION

Figure 2:
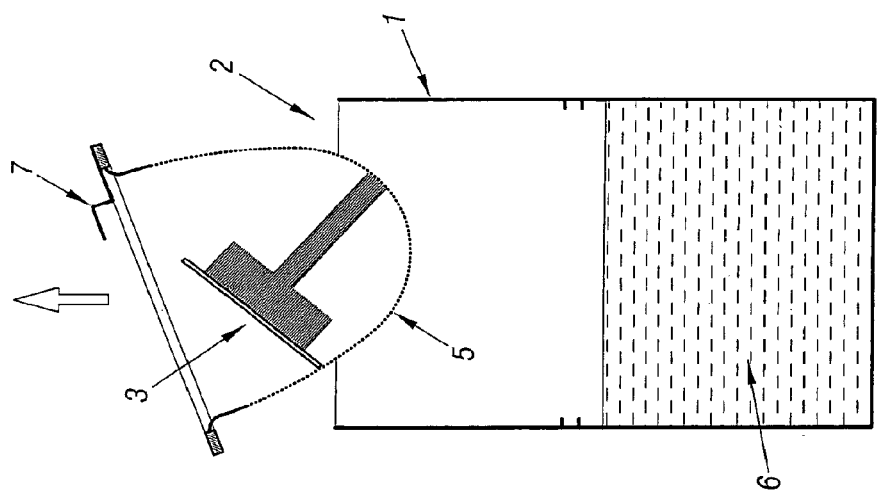
FIGS. 1 and 2 are diagrammatic section views of a first embodiment of a flask of the invention.
Figure 1:
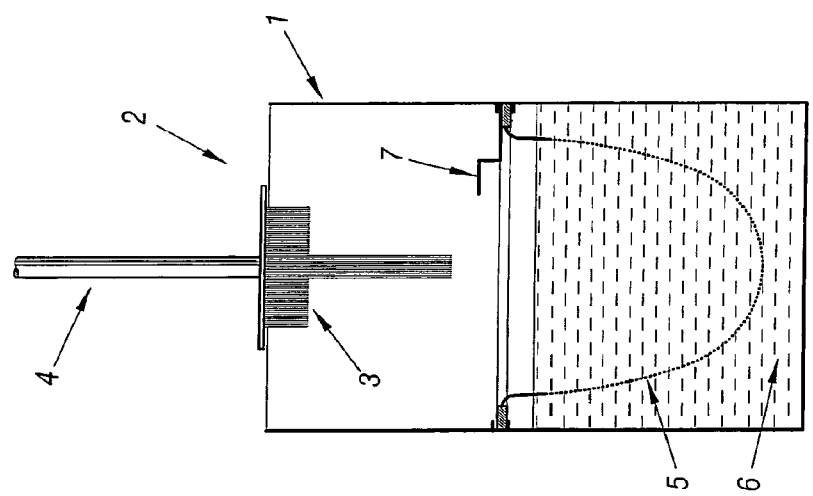

FIGS. 1 and 2 show a first embodiment of a flask of the invention.

This flask is a flask for preparing a cytological suspension based on a fixing solution.

The flask is given overall reference 1 and thus comprises an opening given overall reference 2 suitable for passing a cytological sample-taking brush given overall reference 3 that is detachably fastened to a handle given overall reference 4.

According to the invention, the flask includes a first filter basket for receiving the brush, which basket is at least partially immersed in the suspension.

The basket is made of any suitable filter material, and is given overall reference 5 in FIGS. 1 and 2, and the suspension is given overall reference 6.

The filter basket is also provided with abutment means 7, e.g. formed by a projecting portion thereof that is of hook shape or of some other shape, enabling the brush to be detached from the sleeve, and allowing the brush to drop into the basket, and thus into the suspension.

In the embodiment shown in FIGS. 1 and 2, the filter basket 5 is detachably fastened to the inside of the flask so as to enable it to be withdrawn together with the brush, thus allowing the suspension to be recovered.

Thus, for example, the basket may be screwed into the flask or the basket and the flask may include spring catch means enabling the basket to be withdrawn together with the brush from the flask, as shown in FIG. 2.

All of the undesirable components are then retained by the filter basket so that after it has been withdrawn, the suspension can be recovered.

Figure 4:
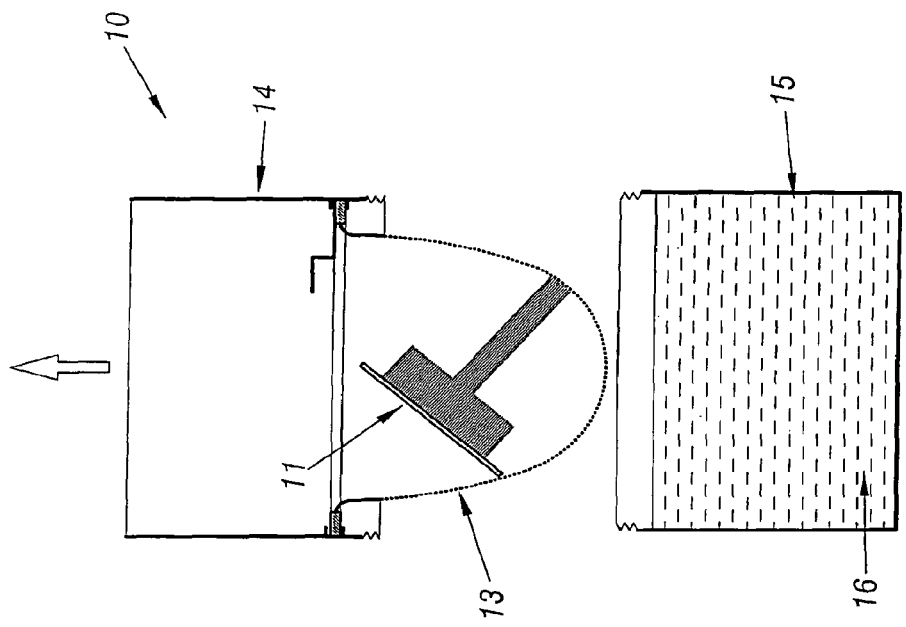
FIGS. 3 and 4 are diagrammatic section views of a second embodiment of a flask of the invention.
Figure 3:
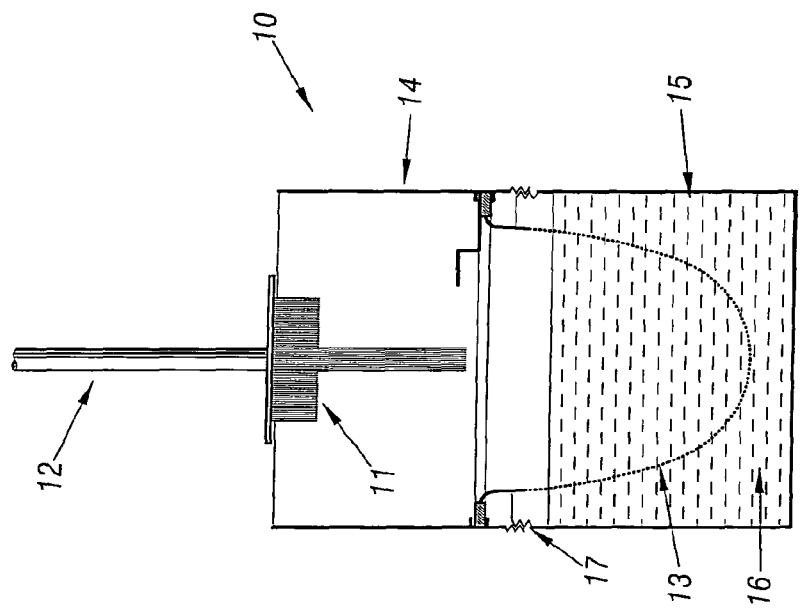

Naturally, other embodiments could be envisaged, such as the embodiment shown in FIGS. 3 and 4.

In these figures, the flask is given overall reference 10, the brush overall reference 11, the handle overall reference 12, and the brush-receiving filter basket overall reference 13.

In this embodiment, the flask comprises two portions that are releasably secured to each other, and given respective overall references 14 and 15.

The basket 13 is then connected to the top portion 14 of the flask while the suspension 16 is contained in the bottom portion of the flask which is given overall reference 15.

These two portions of the flask are releasably secured to each other, e.g. by complementary screw fastener means given overall reference 17, that are provided in the top of the bottom portion 15 and in the bottom of the top portion 14 of the flask.

The suspension is then recovered by unscrewing the bottom portion 15 of the flask, as shown in FIG. 4.

Figure 5:
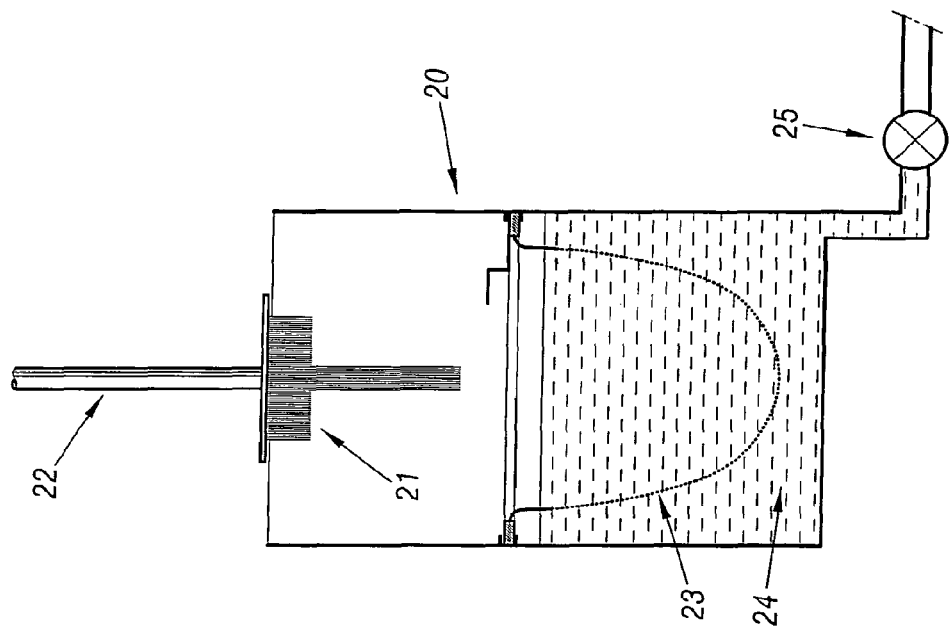

FIG. 5 shows another embodiment in which there can be seen a flask 20, a brush 21, a handle 22, a filter basket 23, and a suspension 24.

In this embodiment, the bottom of the flask is provided with means for draining out the suspension, given overall reference 25, and formed, for example, by valve-forming means that can be actuated by a user in order to recover the suspension by causing it to flow out.

Figure 6:
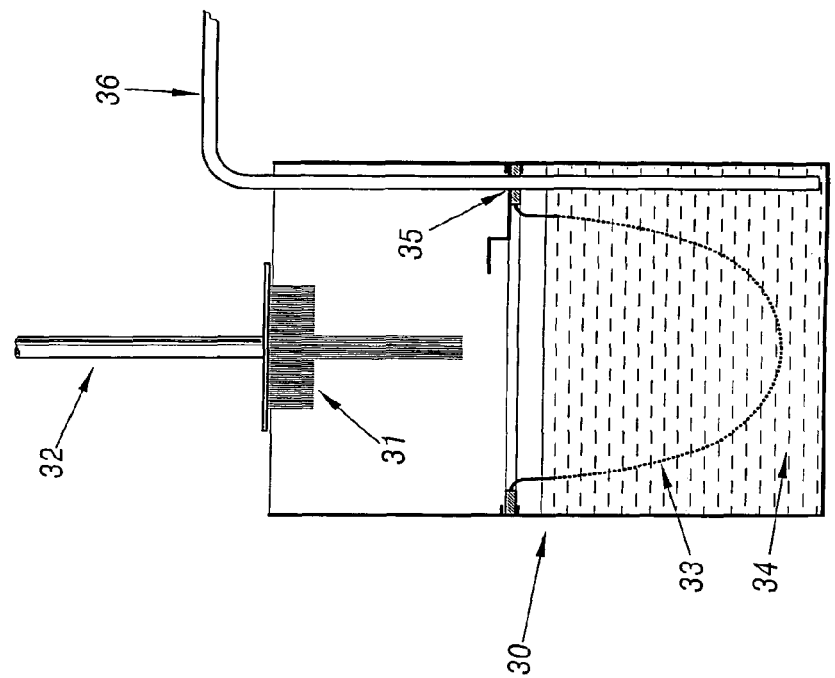
FIGS. 5 and 6 are diagrammatic section views respectively of third and fourth embodiments of a flask of the invention.

Finally, FIG. 6 shows another embodiment in which the flask is given overall reference 30, the brush reference 31, the handle reference 32, the filter basket reference 33, and the suspension reference 34.

In this embodiment, a portion of the filter basket 33 lies outside the suspension 34 and includes a hole for recovering suspension by pouring or by suction.

By way of example, this hole is given overall reference 35 and enables a suction pipe or a pouring pipe, e.g. a pipe 36 to pass therethrough for the purpose of recovering the suspension 34.

Naturally, still other embodiments could be devised.

What is claimed is:

1. A system for preparing a cytological suspension, the system comprising:
    a fixing solution;
    a cytological sample-taking brush detachably fastened to a handle, the cytological sample-taking brush configured for having collected cells; and
    a flask including a filter basket configured for receiving said cytological sample-taking brush with the collected cells, said filter basket being configured to be positionable within the flask so as to be at least partially immersed in the fixing solution to form the cytological suspension, and the cytological suspension can pass through the filter basket, the flask having an opening for receiving said cytological-sample taking brush, a bottom portion of the flask being provided with a valve configured for recovering the cytological suspension,
    the filter basket comprising an abutment configured for detaching the cytological sample-taking brush from the handle, whereby the cytological sample-taking brush drops into the filter basket and into the suspension whereby the collected cells pass through the filter basket and remain in the cytological suspension, said abutment being formed by a projecting portion of said filter basket.

2. The system according to claim 1, wherein the filter basket is detachably fastened inside the flask and is configured to be withdrawn from the flask thereby enabling the cytological sample-taking brush, detached from the handle, to be withdrawn and the cytological suspension to be recovered.

3. The system according to claim 1, wherein the filter basket is screwed into the flask.

4. The system according to claim 1, wherein the filter basket and the flask are configured to enable the filter basket to be withdrawn together with the cytological sample-taking brush.

5. The system according to claim 1, wherein the flask comprises two portions secured to each other in a detachable manner, wherein a top portion connects to the filter basket, and a bottom portion contains the cytological suspension to be recovered.

6. The system according to claim 5, wherein the two portions of the flask have complementary screw fasteners for securing to each other in a detachable manner.

7. The system according to claim 1, wherein the filter basket is configured to be positionable within the flask so that a portion of the filter basket is outside the cytological suspension and said portion outside the cytological suspension has a hole through which the cytological suspension can be recovered.

8. The system according to claim 7, wherein the cytological suspension can be recovered by pouring or by suction.

9. The system according to claim 7, wherein the hole is fitted with a suction pipe or a pouring pipe.

10. The system according to claim 1, wherein the abutment projects inside the filter basket.

11. The system according to claim 1, wherein the abutment is located at a top inside of the filter basket and projects over the filter basket.

12. The system according to claim 11, wherein the abutment is in the shape of a hook.

13. The system according to claim 1, wherein the filter basket is configured so that all undesirable components are retained by the filter basket after the filter basket has been withdrawn from the suspension.

14. The system according to claim 1, wherein the bottom portion of the flask is provided with a valve for recovering the suspension.

\* \* \* \* \*